United States Patent [19]

Hori

[11] 4,287,895

[45] Sep. 8, 1981

[54] ELECTROPALATOGRAPH

[75] Inventor: Kiyoharu Hori, Hino, Japan

[73] Assignee: Rion Co., Ltd., Tokyo, Japan

[21] Appl. No.: 127,932

[22] Filed: Mar. 7, 1980

[30] Foreign Application Priority Data

Mar. 15, 1979 [JP] Japan .................................. 54-29328
Mar. 15, 1979 [JP] Japan .................................. 54-29329

[51] Int. Cl.³ .............................................. A61B 5/10
[52] U.S. Cl. ..................................... 128/777; 128/782; 434/185
[58] Field of Search ................ 128/777, 782; 434/185, 434/112

[56] References Cited

U.S. PATENT DOCUMENTS

| | | | |
|---|---|---|---|
| 3,800,782 | 4/1974 | Josephson et al. | 128/777 |
| 4,112,596 | 9/1978 | Fletcher et al. | 128/777 |
| 4,175,338 | 11/1979 | Takinishi et al. | 128/177 |

FOREIGN PATENT DOCUMENTS 1472067  4/1977  United Kingdom ............... 434/185

OTHER PUBLICATIONS

Fletcher, S. G. et al., *J. Speech & Hearing Research*, vol. 18, No. 4, Dec. 1975.

*Primary Examiner*—Kyle L. Howell
*Attorney, Agent, or Firm*—Leydig, Voit, Osann, Mayer & Holt, Ltd.

[57] ABSTRACT

An electropalatograph wherein a plurality of signal-transmitting electrodes on an artificial palate for detecting linguapalatal contact pattern are scanned sequentially in a predetermined order with a series of scanning signals, transmitted signals from actually contacted ones of the signal-transmitting electrodes to a single signal-receiving electrode on the artificial palate and contacting with the user's hard palate are sequentially detected by a single detector, and detected signals identifying the actually contacted electrodes are employed to dynamically indicate the pattern. To increase detection accuracy, the detected signals are compared with standard linguapalatal contact data, optionally with a modification of such data to provide an allowance in accuracy determination.

15 Claims, 10 Drawing Figures

ELECTROPALATOGRAPH

This invention relates generally to electropalatograph equipments and, more particularly, to improvements in the electropalatograph for observing linguapalatal contact patterns.

Generally, the electropalatograph is a means for electrically dynamically investigating contacting pattern of a speaker's tongue with his hard palate during speeches or phonations with a use of an artificial palate, for the purpose of training speaking ability of persons having a hearing disorder, carebral paralysis or phonation disorder due to such disorder as palatoschisis and the like. There have already been suggested various acoustic or phonometric type voice observing means, but in these means such acoustic characteristic elements of the voice as pitch frequencies, formants, frequency characteristics, their time shifts and the like must be detected and subjected to their self-correlation or mutual-correlation treatment. In addition, considerations must be made of such various conditions that the respective acoustic characteristic elements vary to a large extent depending on the age, sex and so on of individual persons tested or speech-trained, the respective elements detected must be provided, therefore, with a difference in weight in order to obtain optimum results, and so on. For these reasons, such acoustic type means have been made defective in that their structure and operation are complicated and their manufacturing costs are high. On the other hand, the electropalatographs are considered advantageous in the above respects, primarily, as compared with the acoustic type means since the dynamic contacting pattern of the tongue with the hard palate is directly detected and made observable. In the electropalatographs suggested heretofore, however, a plurality of electrodes provided on the artificial palate for sensing the contacting pattern of the tongue with the palate are utilized as signal receiving electrodes while a single electrode brought into contact with the hard palate is employed as a signal transmitting electrode to transmit signals through the tongue to the plurality of signal receiving electrodes, and a plurality of signal detectors are required to be connected respectively to each of the signal receiving electrodes to determine with which receiving electrodes the tongue has contacted, so that the structure of the electropalatographs will be kept still complicated and expensive. The present invention has been suggested to solve such problems as above in the conventional phonometric and palatographic type voice observing means.

A primary object of the present invention is, therefore, to provide an electropalatograph which is remarkably simple in the structure and is thus economical while a high reliability is still maintained.

A further object of the present invention is to provide an electropalatograph which is easy to operate and is still highly reliable.

A yet further object of the present invention is to provide an electropalatograph which can be operated with a high safety.

Another related object of the present invention is to provide an electropalatograph which allows with a remarkably simplified arrangement to compare dynamic linguapalatal contact patterns of a person to be speech-trained with standard linguapalatal contact patterns.

Yet another object of the present invention is to provide an electropalatograph which allows with simplified arrangement and operation to easily additionally compare dynamic linguapalatal non-contact patterns with standard linguapalatal non-contact patterns to achieve an increased reliability of the device.

Another related object of the present invention is to provide an electropalatograph which can achieve phonetic accuracy determination with an optional allowance to perform a gradual speech training with simplified arrangement and operation thereof.

Other objects and advantages of the present invention shall be made clear as the following descriptions of the invention advance in detail with reference to preferred embodiments shown in accompanying drawings, in which:

While the present invention will be detailed with reference to the preferred embodiments as illustrated, the intention is not to limit the invention to the particular embodiments but is to rather include all alterations, modifications and equivalent arrangements possible within the scope of appended claims.

Figure 1:
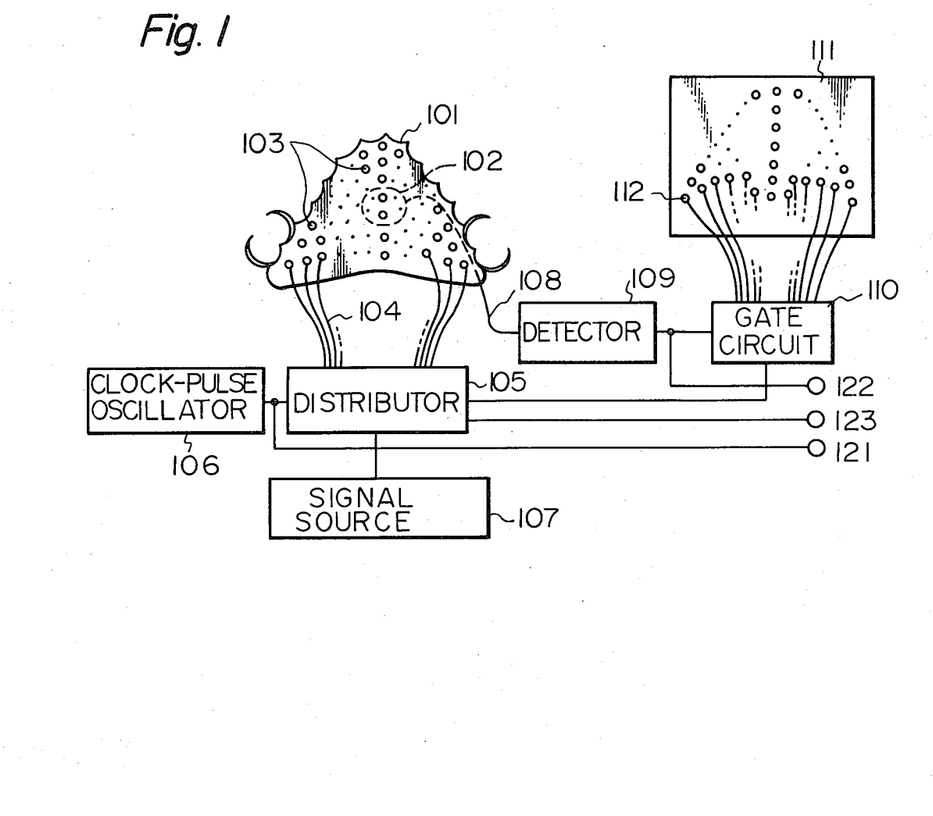
FIG. 1 is a systematic block diagram of an electropalatograph according to the present invention.
Figure 6:
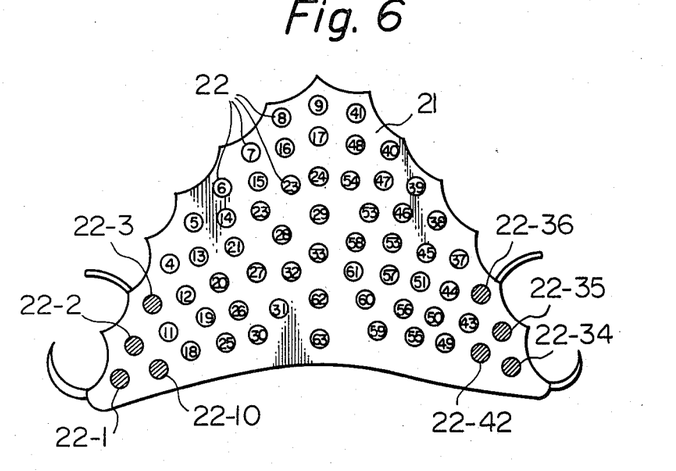
FIG. 6 is an enlarged plan view of the artificial palate for use in the electropalatograph of the present invention for schematically showing an exemplary standard linguapalatal contact pattern of a phonation of [u], similar to that of FIG. 3A, with the respective signal-transmitting electrodes shown as numbered.

Referring now to the systematic arrangement of the electropalatograph of the present invention shown in FIG. 1, an artificial palate 101 made of an insulative material is provided on a surface to be brought into contact with the hard palate of the person speech-trained with a single signal-receiving electrode 102 (the surface is the reverse side of the drawing and the electrode 102 is shown by a dotted line) and on the other surface with which the tongue contacts with a plurality of small signal-transmitting electrodes 103 (the other surface is the front side of the drawing and these electrodes 103 are shown in solid lines), and these signal-transmitting electrodes 103 are distributed substantially evenly over the entire area of said the other surface of the palate 101 as seen most clearly in FIG. 6 where such sequential numbers as 22-1, 22-2, 22-3, . . . are assigned respectively to each of the electrodes 103 so as to predetermine the order in which the electrodes 103 are scanned with a series of signals as will be described later. For this purpose, the respective electrodes 103 are connected through lead wires 104 to respective output terminals of a signal distributor 105 so that output signals of a signal source 107 connected to the distributor 105 will be applied respectively to each of the signal-transmitting electrodes 103 sequentially in the predetermined order of the electrodes as distributed in the distributor 105 in response to clock-pulse signals from a clock-pulse oscillator 106 connected to the distributor 105. The single signal-receiving electrode 102 is connected through a lead wire 108 to a single detector 109 so that an electric voltage of the scanning signals applied to the electrode 102 through the tongue and hard palate from certain ones of the signal-transmitting electrodes 103 with which the tongue contacts during each phonation will be detected by the detector 109. A result of such detection by the detector 109 is provided to a gate circuit 110 which provides its output signals to an indicator 111 in response to the scanning signals from the distributor 105 which are also provided to the gate circuit 110. In the illustrated embodiment, the indicator 111 is provided with a plurality of indicating lamps or light emitting elements 112 disposed substantially in the same arrangement as the signal-transmitting electrodes 103 on the artificial palate 101 so that these lamps 112 will be lighted in response to the result of detection by the detector 109 to indicate the linguapalatal contact patterns dynamically.

Figure 2:
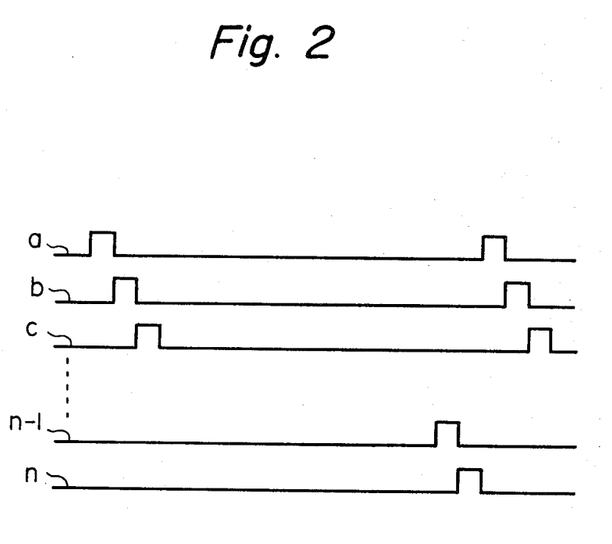
FIG. 2 shows an example of respective signals to be provided respectively to each of signal-transmitting electrodes on an artificial palate used in the electropalatograph of the present invention.
Figure 3A:
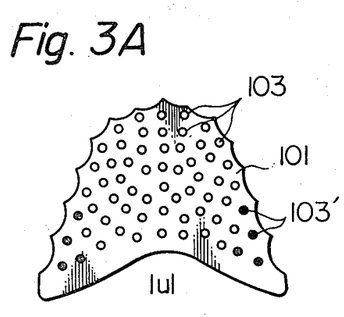
FIGS. 3A through 3E are diagrams showing standard linguapalatal contact patterns at the time of certain typical standard phonations, wherein the signal-transmitting electrodes with which the tongue has contacted are shown as marked dark.
Figure 3B:
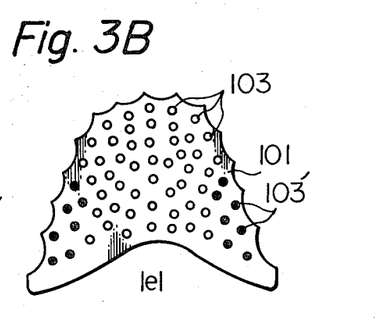
Figure 3C:
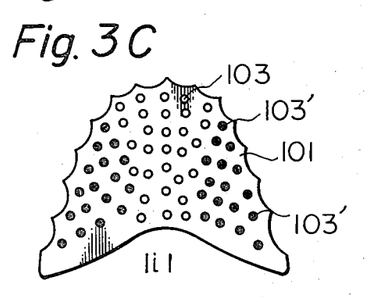
Figure 3D:
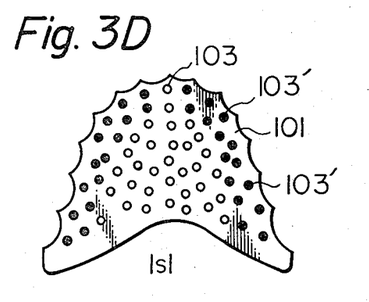
Figure 3E:
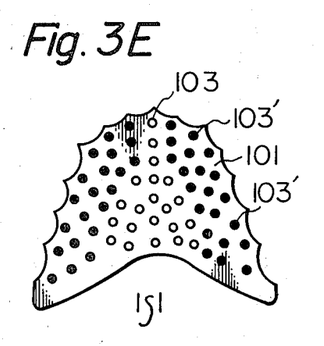

In the above, the distributor 105 and signal source 107 may be substituted by, for example, a ring counter, whereby such scanning signals as shown by wave form diagrams a to n of FIG. 2 can be provided sequentially to the respective signal-transmitting electrodes 103 and also to the gate circuit 110 in the predetermined scanning order for the electrodes 103.

As will be clear from the above, it is easily made possible to visibly indicate on the indicator 111 such dynamic linguapalatal contact patterns of test phonations of the person speech-trained in such patterns as exemplified in FIGS. 3A to 3E showing those of standard phonations of [u], [e], [i], [s] and [ʃ], respectively, wherein the signal-transmitting electrodes 103 with which the tongue has contacted, or corresponding ones of the lamps 112 on the indicator 111, are represented by a reference 103' as hatched, when the series of scanning signals are sequentially presented one by one to each of the signal-transmitting electrodes 103 in the predetermined scanning order of the electrodes 103. This scanning of these electrodes is repeated, and clock-pulse oscillation at the oscillator 106 which is determinative to scanning timing as well as its repetition cycle is properly selected to be of a frequency enough for rendering the indications on the indicator of the certain number of the signal-transmitting electrodes with which the tongue contacts for each phonation during such sequential scanning to be performed substantially momentarily at the same time in the sense of sight.

Figure 4:
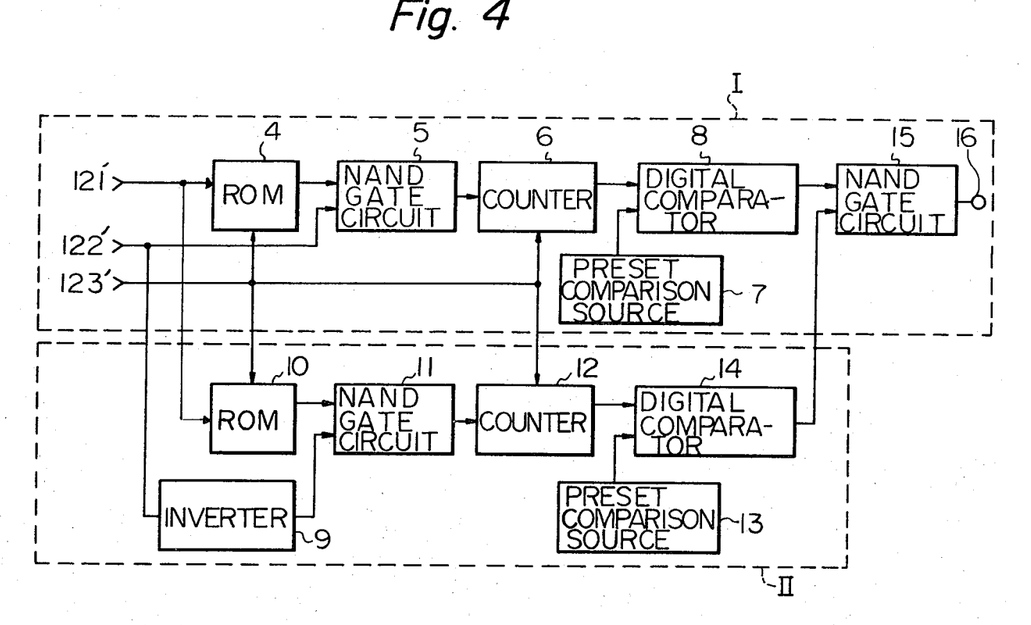
FIG. 4 is a block diagram showing an arrangement to be used with the electropalatograph of FIG. 1 for determining whether phonations of the person being speech-trained are correct or incorrect.

Referring next to an aspect of the present invention as shown in FIG. 4 of an additional circuit arrangement for use with the electropalatograph of FIG. 1 for determining whether the phonations of the person speech-trained are correct or incorrect, the arrangement comprises generally a linguapalatal contact signal treating section I and a linguapalatal non-contact signal treating section II parallel to the section I, respective which comprises the same series connection of a read-only memory (ROM) 4 or 10, NAND gate circuit 5 or 11, counter 6 or 12 and digital comparator 8 or 14 and a preset comparison source 7 or 13 connected to the input side of the digital comparator 8 or 14, respectively, except that an inverter 9 is connected to the input side of the NAND gate circuit 11 in the non-contact signal treating section II.

The ROM 4 or 10 includes storages of a number equal to desired number of phonations for the speech training, each of the storages comprises storage cells of a number equal to that of the signal-transmitting electrodes 103 arranged on the artificial palate which are 63 in the illustrated case of FIG. 6, and in each of the storages a linguapalatal contact signal representative of the respective standard linguapalatal contact patterns for the phonations is stored by means of such storage cells. In reading the stored signals in the ROM, one of the storages which corresponds to a selective phonation is first selected by means of an external switch or the like, then the read is initiated with respect to thus selected storage in response to such signal as shown by a wave form C in FIG. 5 indicative of a termination of each scanning cycle of the distributor 105 and transmitted therefrom through an output terminal 121 of the device of FIG. 1 and an input terminal 121' of the arrangement of FIG. 4 to the respective ROM 4 and 10, and respective bits of the stored signal in the selected storage are sequentially read according to the scanning order of the electrodes 103 in response to the clock-signal pulses such as shown in a wave form A of FIG. 5 which are transmitted from the oscillator 106 through an output terminal 123 and input terminal 123' to the ROM 4 and 10.

In the NAND gate circuit 5, a NAND of the stored signal read out of the ROM 4 and detection result of the detector 109 is taken and is provided to the counter 6. Thus, the counter 6 counts the number of bit or bits of such output signal of the NAND gate 5, that is, any number of the signal-transmitting electrodes 103 in the actual linguapalatal contact pattern which does not coincide with the number of the bits of the stored signal representing the standard linguapalatal contact pattern, for every scanning cycle. The count number of the counter 6 is compared in the digital comparator 8 with the number of the signal-transmitting electrodes 103 in the particular standard linguapalatal contact pattern of the selected phonation (which is 8 in the illustrated case of the phonation [u]) and preliminarily set in the preset comparison source 7, and the comparator 8 provides a signal of high level, that is, "1", only when the both numbers coincide with each other.

In the linguapalatal non-contact signal treating section II, specifically, the detection result of the detector 109 is inverted at the inverter 9 to provide an inverted signal which is indicative of the number of the signal-transmitting electrodes 103 with which the tongue has not contacted during the particular phonation. At the NAND gate circuit 11, therefore, a NAND of the stored signal read out of the ROM 10 thus representing the standard contact pattern of the selected phonation and such inverted signal as above from the inverter 9 is taken, so that the counter 12 will count the number of bits of such output signal of the NAND gate 11, that is, the number of the signal-transmitting electrodes 103 in the actual non-contact pattern which does not coincide with the number of the bits of the stored signal representing the standard non-contact pattern, for every scanning cycle. The count number of the counter 12 is compared in the digital comparator 14 with the number of the electrodes 103 in the standard non-contact pattern of the particular phonation (which is 55 in the illustrated case of the phonation [u]) and preliminarily set in the preset comparison source 13, and the comparator 13 provides a signal of high level "1" only when the both numbers coincide with each other.

A further NAND gate circuit 15 is connected to the output side of the respective digital comparators 8 and 14, so that a NAND of the respective output signals from these comparators 8 and 14 will be taken at the circuit 15, and a low level signal of "0" is provided at an output terminal 16 of the circuit 15 when the selected phonation is correctly made whereas a high level signal of "1" is provided at the terminal 16 when the phonation is incorrectly made. Such output signals can be utilized to easily indicate whether the actual phonation is correct or incorrect.

In the above arrangement, it will be possible to selectively set the values in the preset comparison sources 7 and 13 so that an indication of approximately correct phonations can be made when the actual phonations are rather close to the standard phonations and thereby a progressive or gradual training of speech will be attempted. That is, when it is desired that, while the number of the signal-transmitting electrodes with which the tongue contacts for the standard phonation of [u] is 8, an actual phonation of the same for which the number of electrodes actually contacted is, for example, 6 is to be indicated as being correct, the number "6" may be preset in the preset comparison source 7 so that the comparator 8 will determine that the phonations for which the number of electrodes is in a range of 6 to 8 are correct. In the event when an actual number 53 of the electrodes with which the tongue does not contact is desired to be indicated as being correct, similarly, while the number should be 55 for the phonation of [u], the number "53" may be preset in the preset comparison source 13 so that the comparator 14 will determine that the phonations for which the number of electrodes contacted is in a range of 6 to 10 and that of electrodes non-contacted is in a range of 53 to 57 may be indicated to be correct. Accordingly, it is made possible to put an optional weight on the signal detected by properly selectively modifying the preset number in the preset comparison sources 7 and 13.

Figure 5:
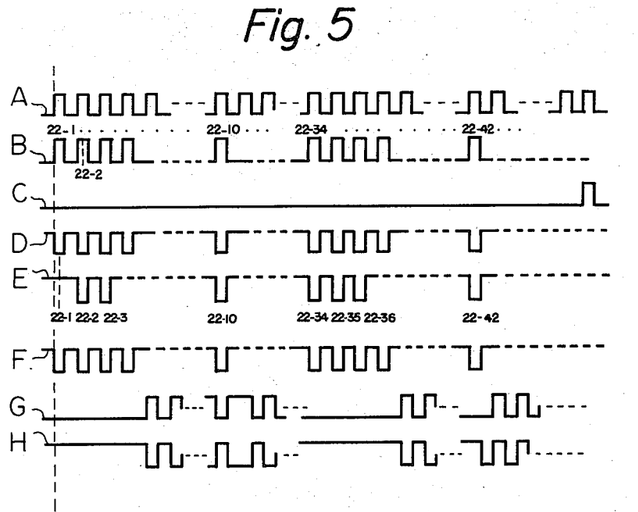
FIG. 5 is a diagram showing input and output wave forms of a NAND gate circuit for explaining the operation of the arrangement of FIG. 4.

The discriminating operation of the arrangement of FIG. 4 shall be further detailed with reference to FIG. 5 which showing the pulse trains representing specifically the signal coincidence of the high level "1" and thus corresponding to such signal-transmitting electrodes with which the tongue contacts for the standard phonation [u] as those indicated by 22-1, 22-2, 22-3, etc. in FIG. 6 which are shown as hatched.

As will be clear from the foregoing descriptions, the stored data of the linguapalatal contact pattern of the selected phonation [u] is provided sequentially from the ROM 4 as signals in response to the clock pulse A upon receiving the signal C denoting the termination of each cycle of the series signals. When a phonation is made by the person speech-trained, such signals as shown by B and identifying actually contacted electrodes are provided from the detector 109 connected to the signal-receiving electrode 102 on the artificial palate, a NAND of the signals B and those from the ROM 4 are taken in the NAND gate circuit 5, and such signals as shown by D are provided from the circuit 5. If the linguapalatal contact pattern of the particular phonation lacks in the contact with, for example, one signal-transmitting electrode 22-1, the output D of the NAND gate circuit 5 will be as shown by E. Similarly, in the other NAND gate circuit 11 of the non-contact signal treating section II, a NAND of the output of the ROM 10 such as shown by G and that of the inverter 9 such as shown by F (which is $\overline{B}$) is taken and the circuit 11 provides signals H.

In the counters 6 and 12, pulse numbers of the signals D (or E) and H which are 8 (or 7) and 55 are counted, respectively, and their counts are provided to the digital comparators 8 and 14, respectively, to have such discriminations as referred to in the foregoings performed therein.

In the foregoing descriptions, it should be appreciated that, while the linguapalatal contact signal and non-contact signal treating sections I and II are provided primarily for the purpose of removing any errors in the detections, either one of these sections may be omitted where such removal is not strictly required and, in this case, a certain modification may be made in the comparison operation of the digital comparator. In this case, further, it should be clear that such means connected to the digital comparator in either section for indicating the dynamic linguapalatal contact patterns as has been referred to may be replaced by any other type of means.

According to the present invention, as has been disclosed in the foregoings, the plurality of signal-transmitting electrodes for detecting the linguapalatal contact pattern are scanned sequentially in a predetermined order by means of a series of scanning signals, the signals transmitted from actually contacted ones of the signal-transmitting electrodes to the single signal-receiving electrode are detected also sequentially by the single detector connected to this signal-receiving electrode, and the thus detected signals identifying the particular electrodes actually contacted by the tongue are employed to dynamically indicate the linguapalatal contact pattern in comparison with the predetermined scanning order of the signal-transmitting electrodes. When the accuracy of the detected signals denoting the actual linguapalatal contact pattern or the optional determination of such accuracy is desired, either or both of the particular detected signals and signals denoting the actual non-contact pattern is compared with either or both of the standard linguapalatal contact and non-contact patterns which are preliminarily sorted with or without any optional weight, and coincidences of thus compared signals are employed to indicate the actual linguapalatal contact pattern. Accordingly, it is made possible according to the present invention to remarkably simplify the structure of the electropalatograph with a result of remarkable reductions in the manufacturing costs while achieving the highly reliable detection and indication, to have the electropalatograph made easily operatable with a high safety, to easily compare the actual linguapalatal contact pattern with the standard linguapalatal contact pattern alone or in combination with the standard non-contact pattern so as to achieve the highly accurate results, and to render the detection and indication achieved irrespective or individual differences in phonetic conditions of the persons to be speech-trained with a selectively preset allowance in the accuracy determination.

What I claim as my invention is:

1. An electropalatograph comprising an artificial palate formed of an insulative material in a configuration substantially coinciding with the hard palate of a person speech-trained, said artificial palate having a plurality of signal-transmitting electrodes distributed substantially over an entire surface of the artificial palate to sense an actual linguapalatal contact during a phonation and a single signal-receiving electrode provided to contact with the hard palate as insulated from said signal-transmitting electrodes, means for scanning sequentially respective said plurality of signal-transmitting electrodes with a series of signals, and means for recognizing a pattern of at least said actual linguapalatal contact on the basis of said scanning signals received by said signal-receiving electrode as transmitted from certain ones of the signal-transmitting electrodes which have sensed the linguapalatal contact.

2. An electropalatograph according to claim 1 wherein said recognizing means includes means for indicating said pattern recognized.

3. An electropalatograph according to claim 1 wherein said recognizing means comprises means for detecting said scanning signals from said signal-receiving electrode, and means for identifying respective said signal-transmitting electrodes which have sensed said linguapalatal contact by comparing sequentially detected signals from said detecting means with said scanning signals from said scanning means.

4. an electropalatograph according to claim 3 which further comprises means connected with said identifying means for indicating said linguapalatal contact pattern in a manner coinciding with distributed pattern of said signal-transmitting electrodes identified by the identifying means.

5. An electropalatograph according to claim 3 wherein said scanning signals comprise a train of periodic pulses, respective said pulses being provided sequentially to respective said signal-transmitting electrodes in accordance with a predetermined order in which the electrodes are arranged.

6. An electropalatograph according to claim 1 wherein said recognizing means includes means for comparing said actual linguapalatal contact pattern with a preliminarily set standard linguapalatal contact pattern for said phonation.

7. An electropalatograph according to claim 6 wherein said comparing means compares said received signals with preliminarily stored standard contact signals corresponding to said signal-transmitting electrodes with which the tongue contacts during a standard phonation of said phonation and read out in response to said scanning signals from said scanning means, counts the number of actually contacted signal-transmitting electrodes denoted by respective said signals compared and at least coinciding with each other, further compares said counted number of contacted signal-transmitting electrodes with a preliminarily set standard number of contacted signal-transmitting electrodes for said standard phonation, and provides an output signal when a difference between respective said numbers compared is at least within a predetermined range.

8. An electropalatograph according to claim 7 wherein said output signal is provided only when said difference is zero.

9. An electropalatograph according to claim 1 wherein said recognizing means includes means for comparing said actual linguapalatal contact pattern with a preliminarily set standard linguapalatal non-contact pattern for said phonation.

10. An electropalatograph according to claim 9 wherein said comparing means obtains signals corresponding to said signal-transmitting electrodes with which the tongue has actually not contacted during said phonation on the basis of said received signals, compares thus obtained signals with preliminarily stored standard contact signals corresponding to said signal-transmitting electrodes with which the tongue contacts during a standard phonation for said phonation and read out in response to said scanning signals from said scanning means, counts the number of said non-contacted signal-transmitting electrodes based on compared result, further compares said counted number of the non-contacted signal-transmitting electrodes with a preliminarily set standard number of non-contacted signal-transmitting electrodes for said standard phonation, and provides an output signal when a difference between respective said numbers compared is at least within a predetermined range.

11. An electropalatograph according to claim 10 wherein said output signal is provided only when said difference is zero.

12. An electropalatograph according to claim 1 wherein said recognizing means includes a first means for comparing said actual linguapalatal contact pattern with a preliminarily set standard linguapalatal contact pattern for said phonation, a second means for comparing an actual linguapalatal non-contact pattern with a preliminarily set standard linguapalatal non-contact pattern for the phonation, and a third means for comparing respective compared results of said first and second comparing means.

13. An electropalatograph according to claim 12 wherein said first comparing means compares said received signals with preliminarily stored contact signals corresponding to said signal-transmitting electrodes with which the tongue contacts during a standard phonation for said phonation and read out in response to said scanning signals from said scanning means, counts the number of actually contacted signal-transmitting electrodes denoted by respective said signals compared and at least coinciding with each other, further compares said counted number of contacted signal-transmitting electrodes with a preliminarily set standard number of contacted signal-transmitting electrodes for said standard phonation, and provides an output signal when a difference between respective said numbers compared is at least within a predetermined range, said second comparing means obtains signals corresponding to said signal-transmitting electrodes with which the tongue has actually not contacted during said phonation on the basis of said received signals, compares thus obtained signals with preliminarily stored standard contact signals corresponding to said signal-transmitting electrodes with which the tongue contacts during the standard phonation and read out in response to said scanning signals from said scanning means, counts the number of said non-contacted signal-transmitting electrodes based on compared result, further compares said counted number of the non-contacted signal-transmitting electrodes with a preliminarily set standard number of non-contacted signal-transmitting electrodes for the standard phonation, and provides an output signal when a difference between respective said numbers compared is at least within a predetermined range, and said third comparing means provides a discrimination signal for a state of the actual linguapalatal contact pattern in response to a level difference between respective said output signals of said first and second comparing means.

14. An electropalatograph according to claim 13 wherein said discrimination signal is provided upon a presence of said difference.

15. An electropalatograph according to claim 13 wherein said discrimination signal is provided upon an absence of said difference.

* * * * *